(12) United States Patent
Iwase (10) Patent No.: US 9,089,280 B2
(45) Date of Patent: Jul. 28, 2015

(54) IMAGE PROCESSING APPARATUS, IMAGE PROCESSING METHOD, AND PROGRAM STORAGE MEDIUM

(75) Inventor: Yoshihiko Iwase, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 201 days.

(21) Appl. No.: 12/943,684

(22) Filed: Nov. 10, 2010

(65) Prior Publication Data

US 2011/0134393 A1    Jun. 9, 2011

(30) Foreign Application Priority Data

Dec. 8, 2009    (JP) .................................. 2009-278949

(51) Int. Cl.
*A61B 3/10*    (2006.01)
*A61B 3/00*    (2006.01)

(52) U.S. Cl.
CPC ............... *A61B 3/102* (2013.01); *A61B 3/0025* (2013.01)

(58) Field of Classification Search
CPC ............ A61B 3/14; G06T 2207/10101; G06T 2207/30041
USPC ................... 351/206, 205, 221; 600/407, 425
See application file for complete search history.

(56) References Cited

U.S. PATENT DOCUMENTS

| | | |
|---|---|---|
| 2007/0285619 A1 | 12/2007 | Aoki |
| 2008/0234972 A1 | 9/2008 | Tsukada |
| 2009/0033870 A1* | 2/2009 | Hangai et al. ................. 351/206 |
| 2010/0189334 A1* | 7/2010 | Tomidokoro et al. ......... 382/131 |
| 2011/0007270 A1* | 1/2011 | Sarver et al. ................... 351/206 |

FOREIGN PATENT DOCUMENTS

| | | |
|---|---|---|
| JP | 2006-132996 A | 5/2006 |
| JP | 2007-325831 A | 12/2007 |
| JP | 2008-154941 A | 7/2008 |
| JP | 2008-237238 A | 10/2008 |
| JP | 2009-061203 A | 3/2009 |

* cited by examiner

*Primary Examiner* — Mahidere Sahle
(74) *Attorney, Agent, or Firm* — Canon U.S.A., Inc. IP Division (57) ABSTRACT

An image generation unit generates a composite image based on a plurality of two-dimensional tomographic images captured while setting an imaging position in a target eye. A tomographic imaging apparatus captures a volume image based on the set imaging position.

18 Claims, 9 Drawing Sheets

IMAGE PROCESSING APPARATUS, IMAGE PROCESSING METHOD, AND PROGRAM STORAGE MEDIUM

BACKGROUND OF THE INVENTION

1. Field of the Invention

The present invention relates to improving the image quality of a tomographic image of an eye.

2. Description of the Related Art

An eye tomographic imaging apparatus, such as an optical coherence tomography (OCT) apparatus, can be used for three-dimensional observation of a condition inside a retinal layer. Recently, tomographic imaging apparatuses have been drawing attention due to the fact that they are useful in providing more accurate diagnosis of diseases.

Ophthalmological diagnosis employs images such as a volume image for grasping a condition of an overall retinal layer, and a high-quality two-dimensional tomographic image for grasping layers that do not show up in a low-quality tomographic image.

The image quality of a tomographic image obtained by OCT depends on the intensity of the near infrared light incident on a retina. Therefore, to improve the image quality of a tomographic image, it is necessary to increase the intensity of the light irradiated on the retina. However, from a safety perspective, there is a limit to the intensity of the light that can be irradiated on the retina. Consequently, there is a need to generate a high-quality tomographic image while irradiating near infrared light in an intensity range that is not a problem in terms of safety. In response to this need, Japanese Patent Application Laid-Open No. 2008-237238 discusses a technique for generating a tomographic image with little noise by superimposing groups of captured two-dimensional tomographic images over each other.

On the other hand, if a thickness of each layer can be measured from a tomographic image of a retina imaged by OCT, a degree of progress of a disease such as glaucoma, or a post-treatment recovery outlook, can be quantitatively diagnosed. Japanese Patent Application Laid-Open No. 2007-325831 discusses a technique which, in order to quantitatively measure the thickness of these layers, detects a boundary of each layer in the retina from a tomographic image using a computer, and measures the thickness of each layer.

However, in Japanese Patent Application Laid-Open No. 2008-237238, one image is generated from images captured by different scanning lines. Consequently, there is a tradeoff between noise reduction and misregistration of an imaging position. Further, since eyes blink and subject to involuntary movement of fixation, adjacent images are not necessarily similar. Therefore, superimposing adjacent images does not always provide a doctor (hereinafter, sometimes referred to as "technician") with a high quality image at the position which the doctor most wants to view. Moreover, when using a computer to detect the boundary of each layer in the retina from a tomographic image, and to measure the thickness of each layer, there is also a need to increase the accuracy of the layer detection in the tomographic images.

SUMMARY OF THE INVENTION

The present invention is directed to improving an image quality of a tomographic image, and to improving layer detection accuracy.

According to an aspect of the present invention, an image processing apparatus includes an image generation unit configured to generate a composite image based on a plurality of two-dimensional tomographic images captured while setting an imaging position in a target eye, an acquisition unit configured to acquire two-dimensional tomographic images captured based on the set imaging position in order to generate a volume image, and a display control unit configured to display at least either the composite image or the volume image on a display unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

A first exemplary embodiment according to the present invention will now be described with reference to the drawings. An image processing apparatus according to the present exemplary embodiment is characterized by, in imaging of a volume image of a target eye, generating a two-dimensional tomographic image with reduced noise by using tomographic images captured in order to determine an imaging position in a retinal layer. Here, "volume image" refers to a collection of two-dimensional tomographic images.

According to the present exemplary embodiment, a high-quality two-dimensional tomographic image and a volume image that captures a wide range can be acquired in a single imaging operation. Here, "high-quality" refers to an image having an improved signal-to-noise (S/N) ratio compared with a single imaging operation. Further, "high-quality" also refers to an image having an increased amount of information required for diagnosis.

An image processing system including the image processing apparatus according to the present exemplary embodiment will now be described in more detail. In the present exemplary embodiment, a case will be described in which one high-quality two-dimensional tomographic image from ordinary two-dimensional tomographic images and a volume image that captures a wide range are acquired in a single imaging operation.

Figure 1:
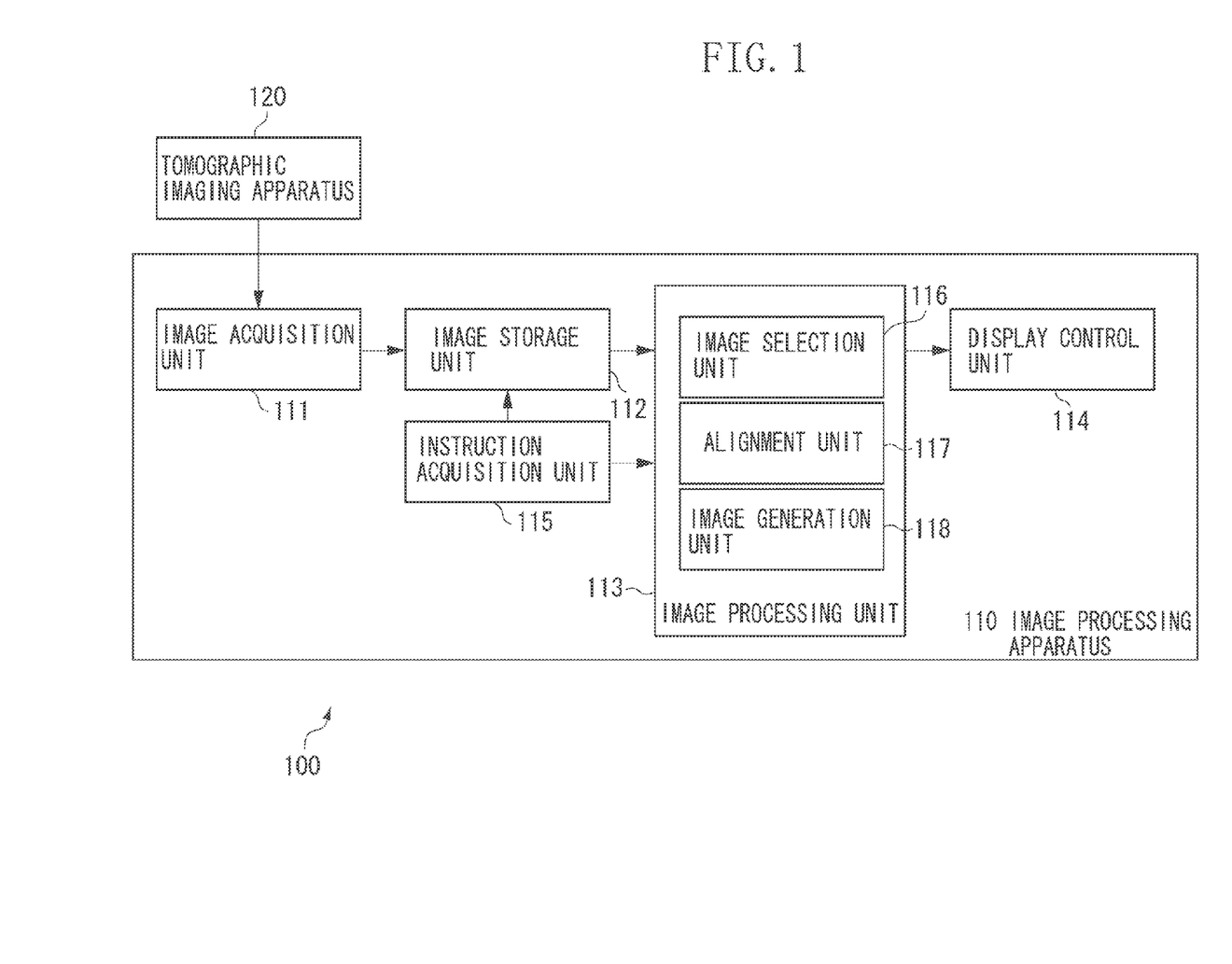
FIG. 1 illustrates a configuration of an image processing system.

FIG. 1 illustrates a configuration of an image processing system 100 including an image processing apparatus 110 according to the present exemplary embodiment. As illustrated in FIG. 1, the image processing system 100 is configured so that the image processing apparatus 110 is connected to a tomographic imaging apparatus 120 via an interface.

The tomographic imaging apparatus 120 is an apparatus for imaging tomographic images of an eye. The tomographic imaging apparatus 120 is configured from, for example, a time domain OCT apparatus or a Fourier OCT apparatus. Since the tomographic imaging apparatus 120 is a conventional apparatus, a detailed description thereof will be omitted here.

The image processing apparatus 110 includes an image acquisition unit 111, an image storage unit 112, an image processing unit 113, a display control unit 114, and an instruction acquisition unit 115.

The image acquisition unit 111 acquires a tomographic image captured by the tomographic imaging apparatus 120, and stores the acquired tomographic image in the image storage unit 112. The image storage unit 112 stores the tomographic images separately based on whether a given tomographic image was captured before or after an imaging instruction from an operator which is acquired by the instruction acquisition unit 115. The image processing unit 113 generates a high-quality two-dimensional tomographic image and a three-dimensional tomographic image from the tomographic images stored separately in the image storage unit 112.

Figure 2:
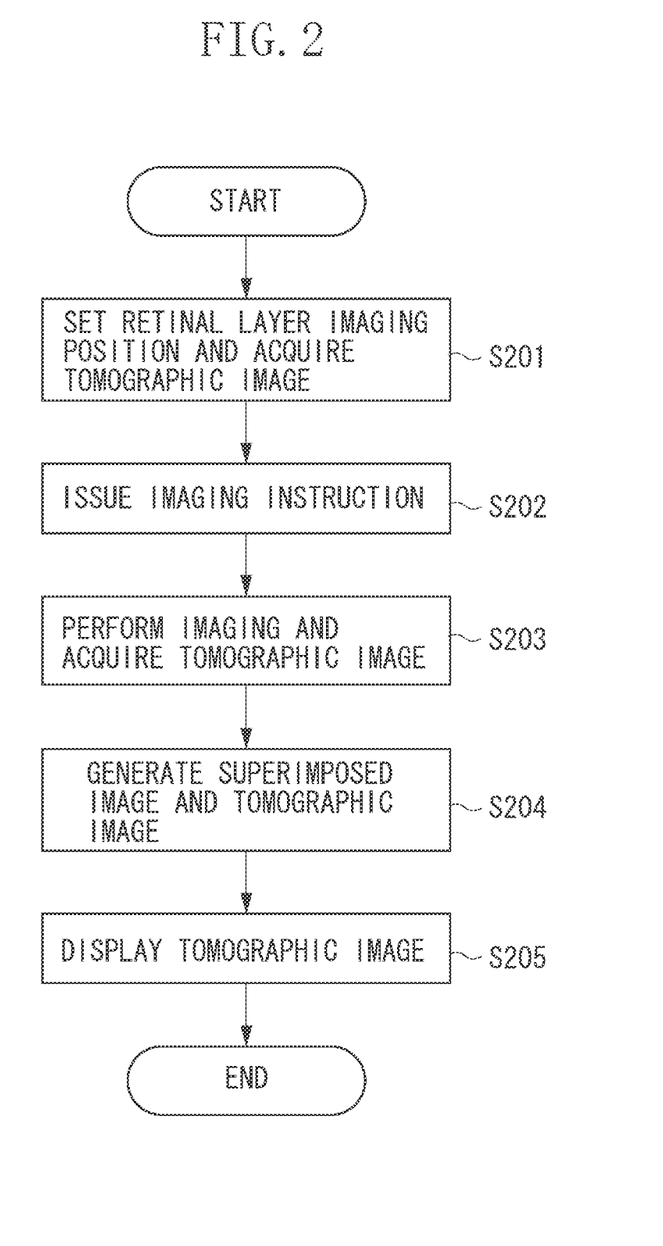
FIG. 2 is a flowchart illustrating a flow of tomographic imaging processing performed by an image processing apparatus.
Figure 3A:
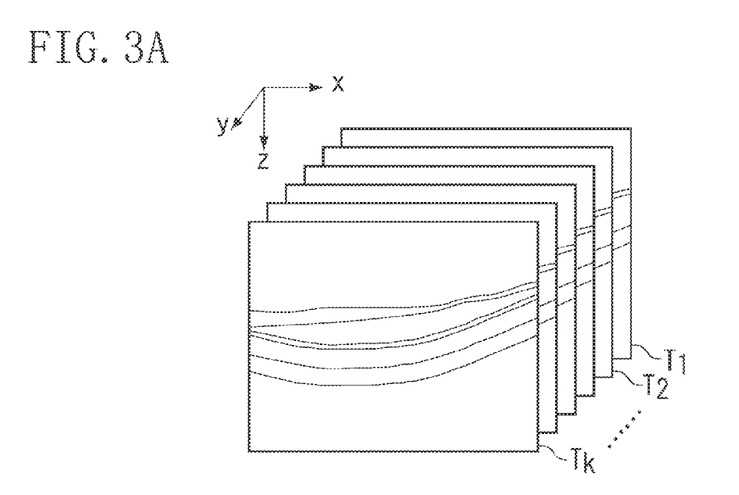
FIGS. 3A to 3C illustrate a volume image and tomographic image generation processing.

FIG. 3A is a schematic diagram illustrating a macular portion volume image of the retina imaged by the tomographic imaging apparatus 120. In FIG. 3A, T1 to Tk are two-dimensional tomographic images of the macular portion. More specifically, the volume image is formed by aggregating two-dimensional tomographic images that captured different locations. Next, a processing procedure performed in the image processing apparatus 110 according to the present exemplary embodiment will be described with reference to FIG. 2.

In step S201, to image the retinal layer, a position of a target eye in a planar direction (x-y plane in FIG. 3A) and in a depth direction (z direction in FIG. 3A) is adjusted by a not-illustrated control unit. Here, the depth direction alignment corresponds to alignment of a coherent gate for obtaining the tomographic image.

Figure 5:
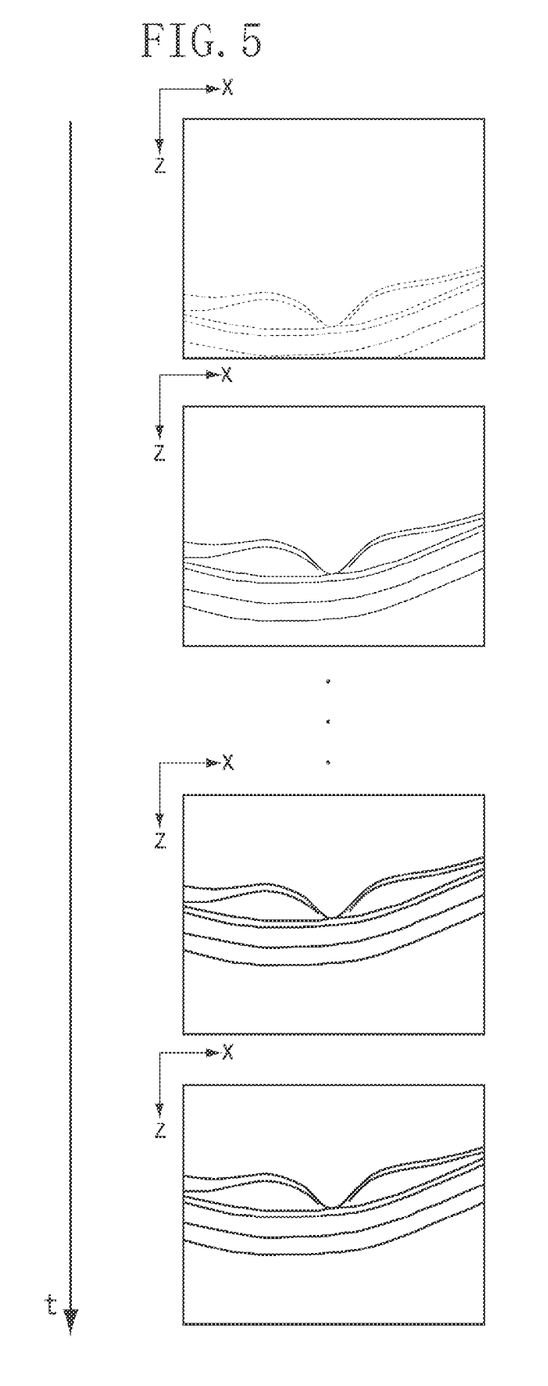
FIG. 5 illustrates setting of an imaging position for a retinal layer in a tomographic image.

While the operator is performing retinal layer alignment, the tomographic imaging apparatus 120 continues to repeatedly scan the same location, and a two-dimensional tomographic image of the same location is displayed on a not-illustrated display unit. The operator adjusts the position in the planar and depth directions while looking at the displayed two-dimensional tomographic image. FIG. 5 illustrates how imaging is performed by adjusting the retinal layer to a desired position in the two-dimensional tomographic image. A vertical axis represents time t. By adjusting the position of the retinal layer with a not-illustrated control unit, the S/N ratio of the tomographic image increases.

In the image storage unit 112, tomographic images from before and after the instruction acquisition unit 115 acquires an instruction to start imaging are stored separately. Usually, the doctor (technician) starts imaging once the two-dimensional tomographic image shown on the display unit settles down at the desired position. Therefore, the images captured before imaging is started get closer and closer to the desired position as the imaging start timing approaches. Thus, imaging starts once the two-dimensional tomographic image settles down at the desired position.

Next, the setting of the imaging position in the retinal layer and the acquisition of the tomographic images from the retinal layer will be described in more detail using FIGS. 4A and 4B.

Figure 4A:
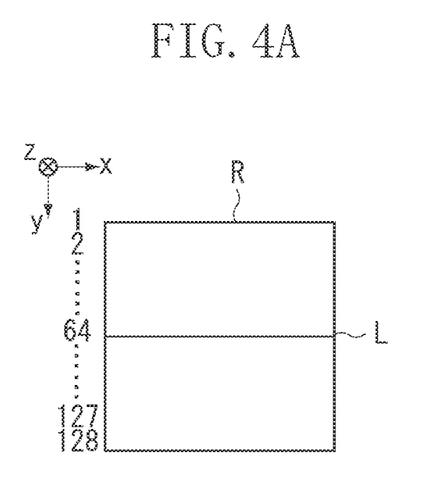
FIGS. 4A and 4B illustrate a range for performing imaging and positions where imaging is performed before and after an imaging instruction.

FIG. 4A is a view of the volume image in FIG. 3A as seen along the x-y plane. In FIG. 4A, R represents a range for imaging the volume image, and L represents a position that the tomographic imaging apparatus 120 repeatedly scans the same location of the target eye while the operator is aligning the retinal layer. A value written on the left side of the imaging range R represents the number of the position for imaging the two-dimensional tomographic image. Here, a vertical resolution (y direction) of the volume image is 128, and the location repeatedly imaged is the 64th position, while is in the middle. An example will now be described in which the retinal layer alignment is performed while the operator is viewing the tomographic images obtained by repeated imaging.

Figure 4B:
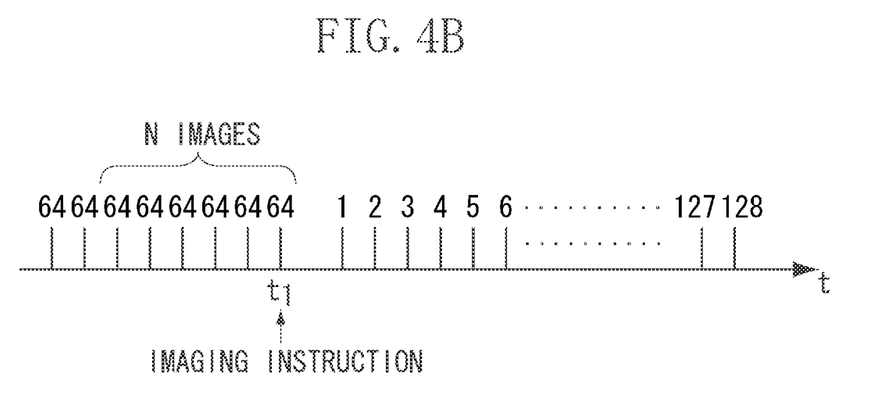

FIG. 4B illustrates the number of the position for a volume image that is captured before and after the imaging instruction. In FIG. 4B, a horizontal axis represents time t. FIG. 4B illustrates a case in which the instruction acquisition unit 115 acquires the imaging instruction at a timing t1. The tomographic imaging apparatus 120 continues imaging of the same position (64) until the instruction acquisition unit 115 acquires the imaging instruction. When the imaging instruction is acquired, the tomographic imaging apparatus 120 images a different position (1 to 128) in order.

In step S201, a not-illustrated control unit adjusts the position to a position that is suited to imaging the retinal layer. Then, in step S202, a not-illustrated imaging instruction unit issues an instruction to start imaging.

In step S203, when the operator issues an imaging instruction (at the timing t1 in FIG. 4B), a not-illustrated control unit scans the x-y planes in order, and 128 pieces of two-dimensional tomographic images are captured. Before the imaging instruction, the image acquisition unit 111 acquires the repeatedly-captured tomographic images of the same location in the target eye. After the imaging instruction, the image acquisition unit 111 acquires the captured tomographic images of different locations in the target eye. Consequently, the image storage unit 112 stores the two-dimensional tomographic images from before the imaging instruction separately from those from after the imaging instruction.

The image storage unit 112 does not have to store all of the images from before the imaging instruction. It is desirable to superimpose images from a predetermined duration going back to the imaging instruction timing or a predetermined N pieces of images (FIG. 4B), and store the superimposed image in the image storage unit 112 as a candidate image. This is because the tomographic images from immediately after alignment is started capture a different position than the desired position, and the images from immediately before performing the imaging instruction capture roughly the same position as the desired position.

In step S204, using the tomographic images stored in the image storage unit 112, the image processing unit 113 generates a high-quality two-dimensional tomographic image and a volume image that captures a wide range. First, the processing for generating a high-quality two-dimensional tomographic image based on superimposition processing will be described.

An image selection unit 116 selects images satisfying a predetermined condition from among N pieces of two-dimensional tomographic images from before the imaging instruction start which are stored in the image storage unit 112. First, tomographic images which include blinking or vignetting are removed from the candidate images to be superimposed. In this case, if imaging is still proceeding, it is desirable that such an image is deleted from the image storage unit 112. This is to reduce the number of unnecessary images so that more useful images can be kept. Further, if the number of images satisfying the predetermined condition is small, the image selection unit 116 may extend the predetermined duration going back to the imaging instruction timing, or increase the number of stored images. Consequently, chances of selecting an image close to the image at the imaging time increase, which leads to improved image quality.

An example of a method for removing these images is to measure the S/N ratio of the two-dimensional tomographic images, and remove those images equal to or less than a threshold Th1. Another method is to perform binarization at a threshold Th2, and remove the two-dimensional tomographic images in which an area equal to or greater than the threshold is less than or equal to a fixed value. The threshold is set in advance based on the characteristics of the tomographic imaging apparatus 120. Alternatively, the threshold may be dynamically set using a discrimination analysis method or a P-Tile method for each target eye.

Next, a reference image is selected. In the present exemplary embodiment, as the reference image, the most recently captured image is used. When the imaging instruction is received, the most recent image is the image at the timing t1 in FIG. 4B. However, if the image at that point was removed because of blinking or the like, the tomographic image captured last among the superimposition candidate images (e.g., the tomographic image captured at t1-1) is used as the reference image.

Consequently, the quality of even an image during observation before the imaging instruction start can be improved. Further, in an initial stage of alignment, superimposition is not performed. By increasing the number of images used for superimposition as a predetermined duration proceeds, both an improvement in the S/N ratio and suppression of image blur can be achieved. Further, the apparatus can also be configured so that superimposition is not performed during observation, but is performed after the imaging instruction start.

Next, two-dimensional tomographic images are aligned by an alignment unit 117. The alignment processing may be performed, for example, by defining an evaluation function which represents a degree of similarity between two tomographic images in advance, and transforming a shape of the tomographic images so that a value of this evaluation function is at its optimum. For the evaluation function, for example, a method which performs an evaluation based on a pixel value may be used (e.g., evaluating using a correlation coefficient).

Examples of transformation processing of the tomographic image include translation or rotation using affine transformation, and changing a magnification rate. In the superimposition processing, a tomographic image having an evaluation function value that is equal to or greater than a threshold Th3 is used. More specifically, based on the processing described above, M pieces of images are selected as a superimposed image from among N pieces of superimposition candidate images.

The present exemplary embodiment will now be described based on the assumption that in the superimposition processing of a plurality of tomographic images, the processing for aligning the tomographic images has already been completed.

Figure 3B:
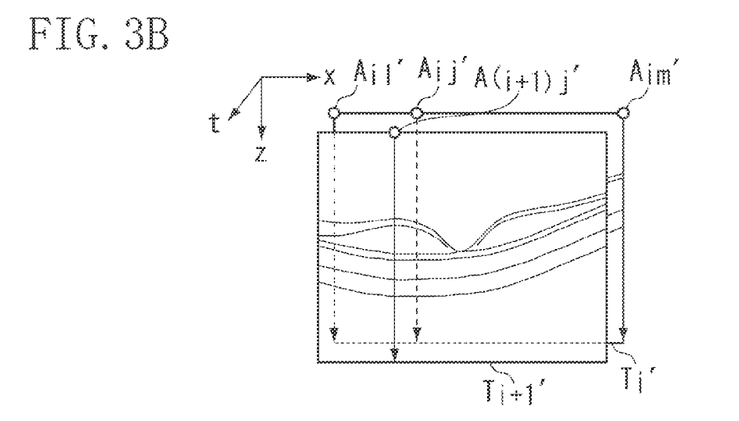
Figure 3C:
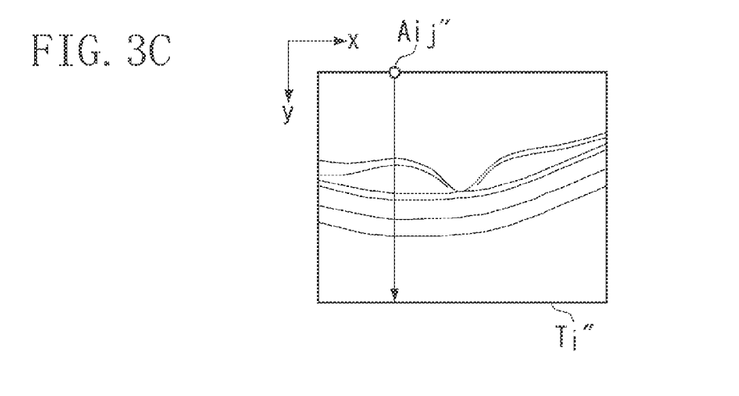

Further, the present exemplary embodiment will be described for a case in which the number of superimposed images M in the same cross-section is two. FIG. 3B illustrates tomographic image generation processing for generating one tomographic image as a composite image by processing a plurality of tomographic images (averaging processing of scanning lines positioned on different tomographic images captured at different times). FIG. 3C illustrates a high-quality two-dimensional tomographic image (composite image) generated by performing averaging processing using M pixels (in the present exemplary embodiment, two pixels) per pixel. More specifically, in FIG. 3C, Aij" is a new scanning line calculated by performing averaging processing on the corresponding scanning lines.

In FIG. 3B, Ti' and Ti+1' are tomographic images captured at different times from the same cross-section. Aij' and A(i+1)' represent the respective scanning lines (A-scan) in the tomographic images Ti' and Ti+1'. The image generation unit 118 performs averaging processing on the scanning lines Aij' and A(i+1)', and calculates the Aij" illustrated in FIG. 3C. The generation processing of the high-quality two-dimensional tomographic image (composite image) is not limited to averaging processing. Methods such as median value calculation processing and weighted average processing may also be used.

Next, the image generation unit 118 generates the volume image illustrated in FIG. 3A based on a plurality of two-dimensional tomographic images from after the imaging instruction which are stored in the image storage unit 112.

In step S205, the display control unit 114 displays at least either the volume image or the high-quality two-dimensional tomographic image generated in step S204 on a not-illustrated display unit.

As can be clearly seen from the above description, in the present exemplary embodiment, a high-quality two-dimensional tomographic image and a volume image that captures a wide range are generated using tomographic images captured to determine the imaging position in the retinal layer.

Consequently, without increasing the imaging time, a high-quality two-dimensional tomographic image and a volume image that captures a wide range can be acquired in a single imaging operation. Therefore, the burden on a patient and on an imaging operator can be lessened. Further, the images used for alignment are captured while the doctor (technician) is viewing them. Therefore, two-dimensional images from the same location are acquired as the end of alignment approaches. Consequently, images having little misregistration can be superimposed, which leads to improved image quality.

In addition, since images can be used that were selected from the two-dimensional images used for alignment, image quality can be improved even further.

Figure 6A:
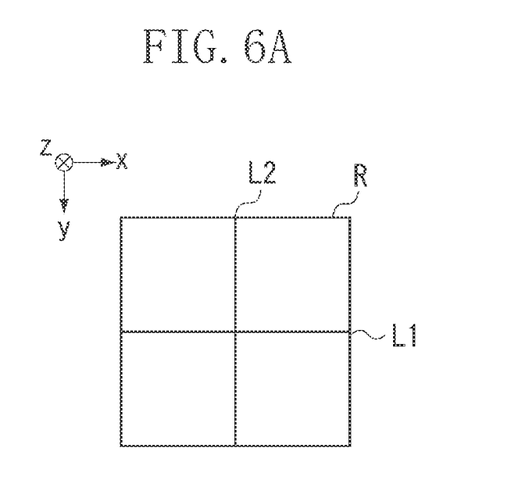
FIGS. 6A and 6B illustrate an example of a scanning line pattern for setting an imaging position.
Figure 6B:
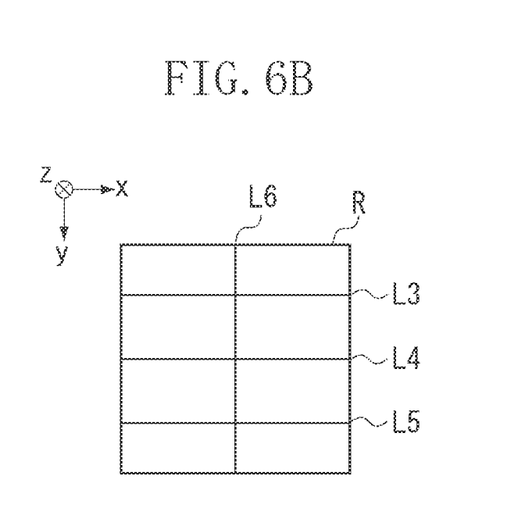

In the present exemplary embodiment, a method for generating a volume image and one high-quality two-dimensional tomographic image is described. However, the present invention is not limited to this method. For example, as illustrated in FIGS. 6A and 6B, a plurality of scanning patterns for performing retinal layer alignment may be used. In FIGS. 6A and 6B, R represents a range for capturing the volume image, and L1 to L6 represent positions that the tomographic imaging apparatus 120 repeatedly scans the same location in the target eye while the operator is performing retinal layer alignment.

The image storage unit 112 separately stores the two-dimensional tomographic images from before the imaging instruction based on the respective scanning position (L1 to L6). By performing the above-described processing at each of these positions, a plurality of high-quality two-dimensional tomographic images can be acquired.

In the above described first exemplary embodiment, a high-quality two-dimensional tomographic image and a volume image that captures a wide range are generated using tomographic images captured for the purpose of determining an imaging position in a retinal layer. However, a second exemplary embodiment is characterized by performing segmentation of the retinal layer using the high-quality two-dimensional tomographic image generated as described above, and then using the obtained result to segment the retinal layer in the volume image.

According to the present exemplary embodiment, segmentation of the volume image is performed by using a result obtained by performing segmentation based on the high-quality two-dimensional tomographic image as an initial value (or a reference). This allows the segmentation of the volume image to be performed highly accurately.

Figure 7:
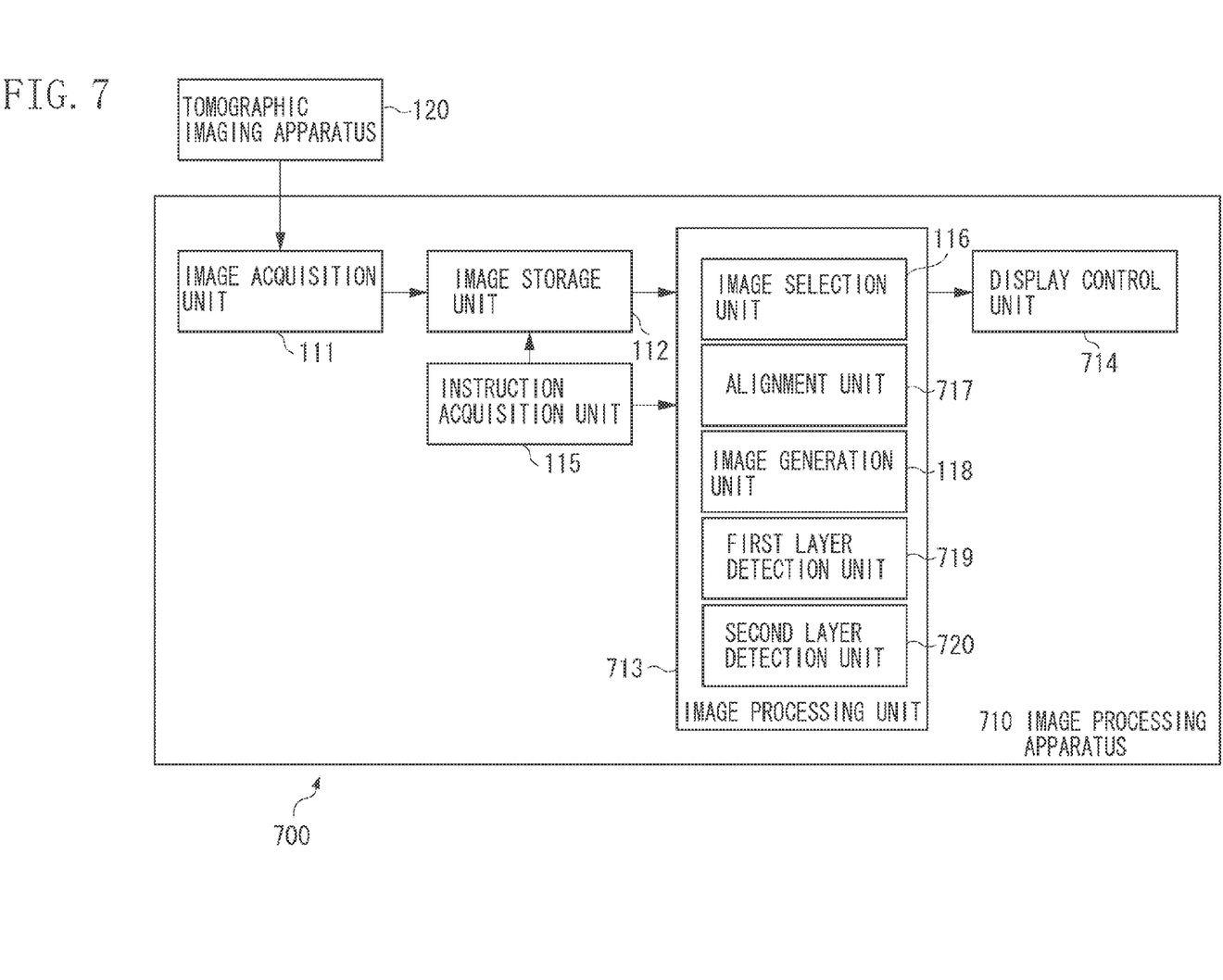
FIG. 7 illustrates a configuration of an image processing system.

FIG. 7 illustrates a configuration of an image processing system 700 which includes an image processing apparatus 710 according to the present exemplary embodiment. As illustrated in FIG. 7, the image processing apparatus 710 includes an image acquisition unit 111, an image storage unit 112, an image processing unit 713, a display control unit 714, and an instruction acquisition unit 115. Other than the image processing unit 713 and the display control unit 714, these units have the same function as in the first exemplary embodiment, and thus a description thereof will be omitted here.

In the image processing unit 713, a first layer detection unit 719 detects the retinal layer from a high-quality two-dimensional tomographic image, and a second layer detection unit 720 detects the retinal layer from a volume image. An alignment unit 717 aligns the result of layer detection that was performed based on the high-quality two-dimensional tomographic image with the volume image.

Figure 8:
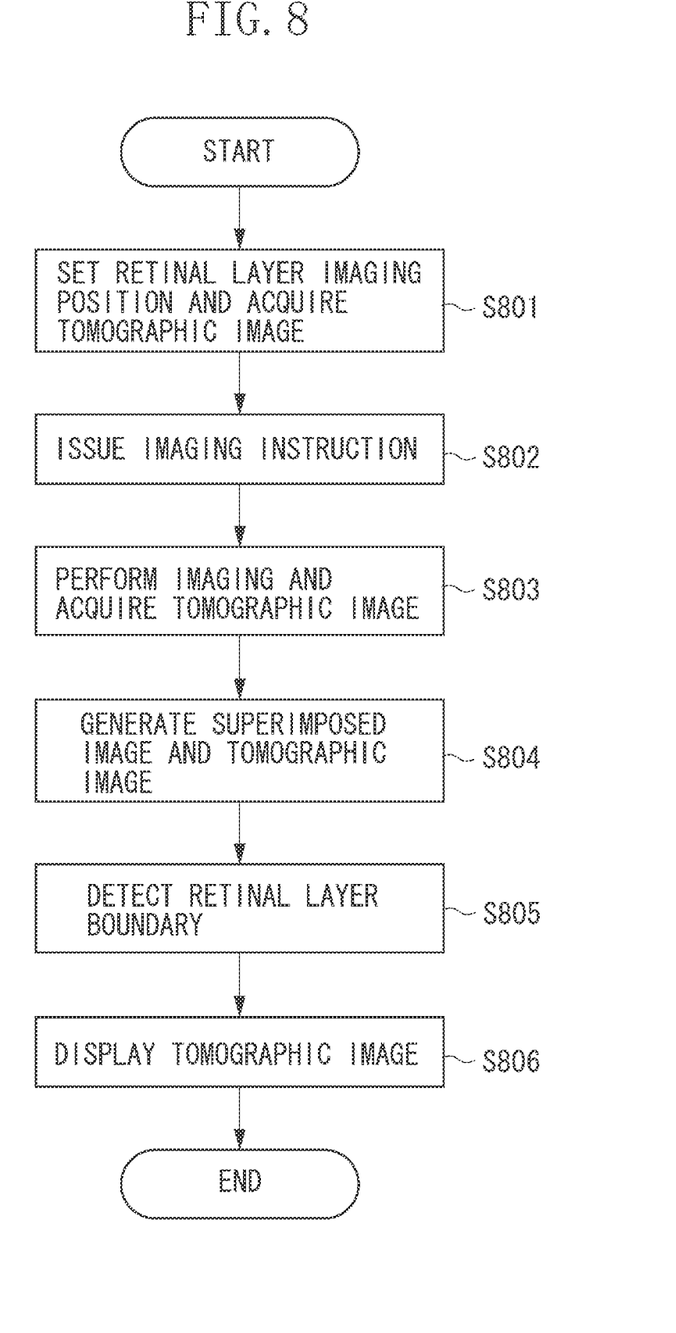
FIG. 8 is a flowchart illustrating a flow of tomographic imaging processing performed by an image processing apparatus.
Figure 9A:
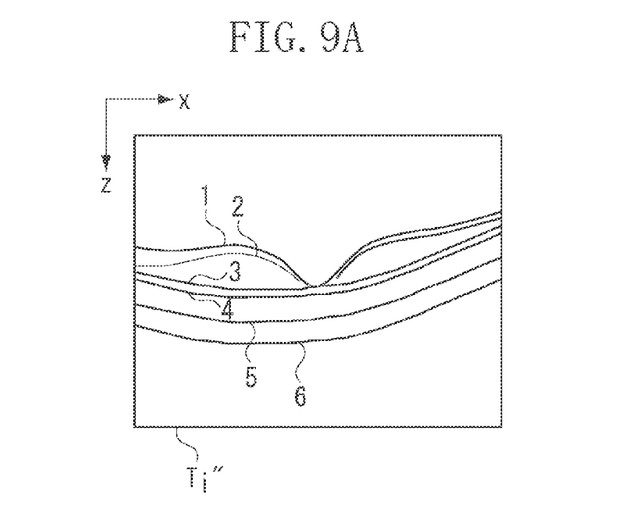
FIGS. 9A and 9B illustrate an example in which a layer detection result is applied in another tomographic image.
Figure 9B:
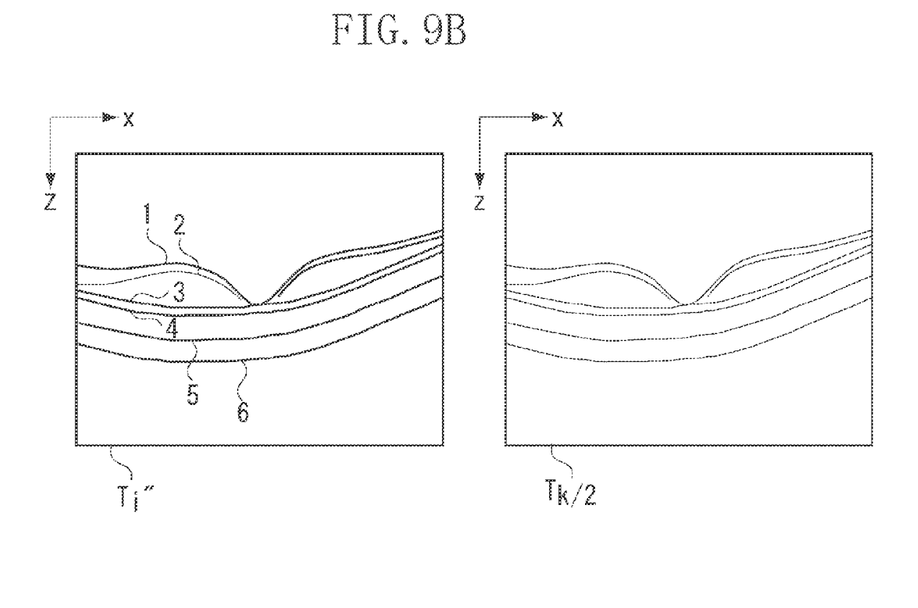

A processing procedure of the image processing apparatus 710 according to the present exemplary embodiment will now be described with reference to FIGS. 8, 9A, and 9B. Other than steps S805 and S807, the processing steps are the same as those of steps S201 to S204 in the first exemplary embodiment, and thus a description thereof will be omitted here.

In step S805, first, the retinal layer is detected from the high-quality two-dimensional tomographic image.

First, the first layer detection unit 719 performs smoothing filter processing on a two-dimensional tomographic image to reduce a noise component. Then, the first layer detection unit 719 performs edge detection filter processing to detect an edge component from the tomographic image and extract an edge corresponding to a layer boundary. Compared with a low-quality tomographic image, in a high-quality two-dimensional tomographic image the noise component is suppressed and signal component in the retinal layer is emphasized. Consequently, the edge component corresponding to the layer boundary can be accurately extracted. The first layer detection unit 719 specifies a background region from the two-dimensional tomographic image in which the edge was detected, and extracts a luminance value characteristic of the background region from the two-dimensional tomographic image. Next, the first layer detection unit 719 determines the boundary of each layer using a peak value of the edge component and an inter-peak luminance value characteristic.

For example, the first layer detection unit 719 searches for an edge from a vitreous body side in a depth direction of an eye fundus, and determines the boundary between the vitreous body and the retinal layer based on a peak of the edge component, the luminance characteristic above and below that edge component peak, and the background luminance characteristic. In addition, the first layer detection unit 719 searches for an edge in the depth direction of the eye fundus, and determines a retinal pigment epithelial layer boundary based on a peak of the edge component, the inter-peak luminance characteristic, and the background luminance characteristic. Based on the above processing, the layer boundary can be detected. This state is illustrated in FIG. 9A. FIG. 9A illustrates each of the boundaries (1 to 6) in the retinal layer detected from a high-quality two-dimensional tomographic image Ti". When performing layer detection based on the volume image, the layer boundary results illustrated in FIG. 9A will be referenced.

To apply the layer detection result acquired from the two-dimensional tomographic image in the volume image, the alignment unit 717 performs alignment processing. The alignment processing will be described using FIG. 9B. FIG. 9B illustrates a high-quality two-dimensional tomographic image Ti" and a tomographic image Tk/2 that captures the center of the volume image.

In the present exemplary embodiment, the high-quality two-dimensional tomographic image Ti" is generated from a group of tomographic images that captured a position corresponding to the center of the volume image, which were captured before the volume image was captured. However, since eyes slightly move due to involuntary movement of fixation and the like, an optimum position is selected by aligning a plurality of tomographic images from near the center of the volume image. As the alignment method, the method described in step S204 of the first exemplary embodiment is used, and thus a description thereof is omitted here. The retinal layer detection result of the two-dimensional tomographic images (boundaries 1 to 6 in FIG. 9B) is superimposed on the tomographic image that has the highest evaluation value among the plurality of tomographic images from near the center of the volume image.

Next, the second layer detection unit 720 detects the retinal layer from the volume image. First, the second layer detection unit 720 performs smoothing filter processing on the volume image to reduce a noise component. Then, the second layer detection unit 720 performs edge detection filter processing to detect an edge component from the tomographic image and extract an edge corresponding to a layer boundary. Next, using the respective boundaries (1 to 6 in FIG. 9B) in the retinal layer detected by the first layer detection unit 719 as an initial value, the second layer detection unit 720 detects the retinal layer in a single two-dimensional tomographic image in the volume image by searching for the edge in the vertical direction. Alternatively, using the respective boundaries in the retinal layer detected by the first layer detection unit 719 as the initial value, the second layer detection unit 720 detects the retinal layer in a single two-dimensional tomographic image in the volume image by applying an active contour method (e.g., snakes method or level set method).

From a single two-dimensional tomographic image in a volume image that does not have as good an image quality as a high-quality two-dimensional tomographic image, the retinal layer can be accurately detected. Consequently, a characteristic amount for each layer region and a characteristic amount of the background region (average, distribution, standard deviation of the luminance value etc.) can be extracted from the volume image. The second layer detection unit 720 performs retinal layer detection from all of the three-dimensional tomographic images using a thus-determined characteristic amount.

For example, in a tomographic image other than a tomographic image determined based on the initial value, the second layer detection unit 720 searches for an edge from the vitreous body side in the depth direction of the eye fundus. Then, the second layer detection unit 720 determines the boundary between the vitreous body and the retinal layer based on a peak of the edge component, the luminance characteristic above and below that edge component peak, and the background luminance characteristic determined based on a single two-dimensional tomographic image in the volume image.

Alternatively, the second layer detection unit 720 can also detect the retinal layer from the volume image using a method for detecting the layer boundaries based on a technique using graph theory such as Graph-Cut approach. The Graph-Cut approach requires a "seed" as an initial value, the interior of the retinal layer region, in which the retinal layer detection result determined by the first layer detection unit 719 corresponds to the volume image, is used for the initial value (seed) for the Graph-Cut approach. A node corresponding to each pixel in the image and terminals referred to "sink" and "source" are set. Further, an edge (n-link) for linking the nodes to each other and an edge (t-link) for linking the terminal with the node are also set.

Pixels serving as an object region O (object seed) and a background region B (background seed) are set in advance as initial values for Graph-Cut approach. In this case, a pixel in the layer region in which the layer region determined by the first layer detection unit 719 corresponds to the volume image is determined as "O", and the other regions are determined as "B". A layer can be detected by determining the minimum cut in a graph drawn by giving a weight to these edges.

From a tomographic image adjacent to a tomographic image which applied the result from the first layer detection unit 719, the retinal layer is detected using spatial information. In a volume image in which the alignment of adjacent tomographic images has finished, there is a high degree of similarity in the shape of the retinal layer captured among adjacent tomographic images. Consequently, the retinal layer detection result of the tomographic image which applied the result of the first layer detection unit 719 can be applied to adjacent tomographic images.

In the tomographic image which applied the result of the first layer detection unit 719, for a pixel that is some distance away from the boundary between the object and the background, the probability of the object and the background switching is low, even for a pixel in a corresponding adjacent tomographic image. More specifically, for example, if a pixel in the tomographic image which applied the result of the first layer detection unit 719 is the background, the probability that a pixel in a corresponding adjacent tomographic image is the background is high.

Therefore, for a pixel corresponding to the adjacent tomographic image, a t-link cost is set using information that this pixel is the background. Further, for the tomographic image which applied the result of the first layer detection unit 719, for a pixel that is near the boundary between the object and the background, it is not known whether the pixel in the corresponding adjacent tomographic image is the object or the background. Consequently, the t-link cost is set for the pixel corresponding to the adjacent tomographic image using information that there is about an equal probability that the pixel is the object or the background.

Retinal layer detection is performed by applying the above processing to all of the three-dimensional tomographic images.

In step S806, the display control unit 714 displays at least either the volume image or the high-quality two-dimensional tomographic image generated in step S804, and the layer boundaries detected in step S805 on a not-illustrated display unit. An example of the display method is to superimpose the layer boundary over the tomographic image. Another example is to display as a graph alongside the tomographic image. Still another example is to measure a thickness of an arbitrary layer based on the layer detection results, and display the measurement result.

According to the above configuration, the volume image and the high-quality two-dimensional tomographic image can be obtained simultaneously. Therefore, when segmentation of the volume image is performed, the segmentation is performed based on the high-quality two-dimensional tomographic image. Then, using the detection result as an initial value, the volume image is segmented. Consequently, the segmentation of the volume image can be performed accurately.

Further, before starting to capture the volume image as described above, the two-dimensional tomographic images captured for alignment are used for segmentation. Therefore, because positional correlation between the volume image and the two-dimensional tomographic images is high, segmentation of the volume image can be performed more accurately. In addition, the two-dimensional tomographic images used for alignment reflect the position that the technician wishes to observe. Consequently, the technician's intention can also be reflected in the segmentation of the volume image.

In the present exemplary embodiment, the high-quality two-dimensional tomographic image is described as an image generated using tomographic images captured for the purpose of imaging alignment of the retinal layer. However, the present invention is not limited to this configuration. For example, the present invention may also be applied in layer detection referring to a high-quality two-dimensional tomographic image generated from tomographic images obtained by repeatedly imaging the same location after an imaging instruction.

Alternatively, the present invention may be applied in layer detection referring to a high-quality two-dimensional tomographic image generated by reducing a scanning interval (increasing the resolution). In addition, the present invention may be applied in layer detection referring to high-quality two-dimensional tomographic images captured at different time. More specifically, the present exemplary embodiment can be applied as long as a tomographic image can be obtained that has a higher quality than a volume image.

Each of the above described exemplary embodiments realized the present invention as an image processing apparatus. However, the exemplary embodiments according to the present invention are not only limited to an image processing apparatus. The present invention may also be realized as software running on a computer. A central processing unit (CPU) in the image processing apparatus performs overall control of the computer using a computer program and data stored in a random access memory (RAM) or a read-only memory (ROM). Further, the functions of each unit may be realized by causing the image processing apparatus CPU to control execution of the software corresponding to each unit in the image processing apparatus.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-278949 filed Dec. 8, 2009, which is hereby incorporated by reference herein in its entirety.

What is claimed is:

1. An image processing apparatus, comprising:
   a generation unit configured to generate a new two dimensional tomographic image based on a first plurality of two-dimensional tomographic images of an object, the first plurality of two dimensional tomographic images acquired before acquisition of a second plurality of two-dimensional tomographic images of the object, wherein a three-dimensional image of the object is generated based on the second plurality of two-dimensional tomographic images, and wherein the first plurality of two-dimensional tomographic images is acquired while adjusting a position in a depth direction of the object; and
   a display control unit configured to display at least one of the new two-dimensional tomographic image and the three-dimensional image on a display unit.

2. The image processing apparatus according to claim 1, wherein the first plurality of two-dimensional tomographic images are images acquired at an approximately same position in a planar direction in the object before an instruction for acquiring the second plurality of two-dimensional tomographic images, which are used to generate the three-dimensional image of the object, is issued, and the three-dimensional image is an image formed from two-dimensional tomographic images acquired at different positions in the planar direction in the object after the instruction for acquiring the second plurality of two-dimensional tomographic images is issued.

3. The image processing apparatus according to claim 1, further comprising:
   a selection unit configured to select the smallest number of two-dimensional tomographic images from the first plurality of two-dimensional tomographic images wherein the generation unit is configured to generate a new two-dimensional tomographic image by superimposing the plurality of two-dimensional images selected by the selection unit.

4. The image processing apparatus according to claim 1, further comprising:
   a first layer detection unit configured to detect a retinal layer of an eye from a new two-dimensional tomographic image; and
   a second layer detection unit configured to detect the retinal layer from each of the second plurality of two-dimensional tomographic images from which the three-dimensional image is formed based on a detection result by the first layer detection unit.

5. The image processing apparatus according to claim 2, wherein the new two-dimensional tomographic image is an image before an imaging instruction is issued and is an image of a predetermined duration.

6. The image processing apparatus according to claim 2, wherein a number of images to be used to generate a new two-dimensional tomographic image by the generation unit is different between before the instruction is issued and after the instruction is issued.

7. A method for image processing, the method comprising:
   acquiring a first plurality of two-dimensional tomographic images of an object before acquisition of a second plurality of two-dimensional images of the object, wherein a three-dimensional image of the object is generated based on the second plurality of two-dimensional tomographic images and wherein the first plurality of two-dimensional tomographic images is acquired while adjusting a position in a depth direction of the object;
   generating a new two-dimensional tomographic image based on the first plurality of two-dimensional tomographic images; and
   displaying at least one of the three dimensional image and the new two-dimensional tomographic image.

8. The method according to claim 7, further comprising storing the acquired tomographic images of the object.

9. A recording medium storing a program for causing a computer to execute the method according to claim 7.

10. An image processing system in which the image processing apparatus according to claim 1 is communicably connected to an imaging apparatus configured to capture an image of the object, wherein the imaging apparatus captures images of the object and acquires a plurality of two-dimensional tomographic images of the object before a second plurality of two-dimensional images of the object is acquired and the position in the depth direction of the object is adjusted, the second plurality of two-dimensional tomographic images used to generate the three dimensional image.

11. The image processing system according to claim 10, comprising:
    an instruction unit configured to issue an instruction to acquire the second plurality of two-dimensional tomographic images, which are used to generate a three-dimensional image of the object,
    wherein the second plurality of two-dimensional tomographic images are images acquired at an approximately same position in a planar direction of the object before the instruction unit issues an instruction, and
    wherein the second plurality of two-dimensional tomographic images are images acquired at different positions in the planar direction of the object after the instruction unit issues the instruction.

12. The image processing apparatus according to claim 1, wherein the first plurality of two-dimensional tomographic images are images acquired at a predetermined position in the planar direction of the object, and
    wherein the second plurality of two-dimensional tomographic images are images acquired at different positions in the planar direction of the object.

13. The image processing apparatus according to claim 1, further comprising:
    an alignment unit configured to align, with a position in a depth direction of a two-dimensional tomographic image of the first plurality of two-dimensional tomographic images, immediately before the second plurality of two-dimensional tomographic images, which are used to generate the three-dimensional image of the object are acquired, a position in the depth direction of another two-dimensional tomographic image among the first plurality of two-dimensional tomographic images.

14. The image processing apparatus according to claim 1, wherein the generation unit generates the new two-dimensional tomographic image by processing to superimpose the first plurality of two-dimensional tomographic images.

15. The image processing apparatus according to claim 14, wherein the superimposing processing is at least one of averaging processing, median value calculation processing and weighted average processing.

16. The image processing apparatus according to claim 3, wherein the selection unit selects a two-dimensional tomographic image having an image quality evaluation value equal to or greater than a threshold from the first plurality of two-dimensional tomographic images.

17. The image processing apparatus according to claim 4, wherein the second layer detection unit detects a layer of fundus from a first two-dimensional tomographic image acquired at a position corresponding to a position where the new two-dimensional tomographic image is acquired among the second plurality of two-dimensional tomographic images from which the three-dimensional image is formed based on the detection result by the first layer detection unit, and wherein the second layer detection unit detects the layer of fundus from a second two-dimensional tomographic image adjacent to the first two-dimensional tomographic image among the second plurality of two-dimensional tomographic images from which the three-dimensional image is formed based on the detection result.

18. The image processing apparatus according to claim 4, wherein the display unit displays a two-dimensional tomographic image acquired at a position corresponding to a position where the new two-dimensional tomographic image is acquired among the second plurality of two-dimensional tomographic images from which the three-dimensional image is formed, and displays the layer detected from the new two-dimensional tomographic image superimposed over the displayed two-dimensional tomographic image.

* * * * *